(12) United States Patent
Yvin et al.

(10) Patent No.: US 6,921,540 B1
(45) Date of Patent: Jul. 26, 2005

(54) HYPOOSMOTIC SALINE SOLUTIONS, METHOD FOR PREPARING SAME AND MEDICINES BASED ON SAID SOLUTION

(75) Inventors: Jean-Claude Yvin, Saint-Malo (FR); Didier Leroy, Pleurtuit (FR); Olivier Tabary, Reims (FR); Jacky Jacquot, Reims (FR); Edith Puchele, Reims (FR)

(73) Assignee: Laboratoires Goemar SA, Saint Malo (FR)

( * ) Notice: Subject to any disclaimer, the term of this patent is extended or adjusted under 35 U.S.C. 154(b) by 0 days.

(21) Appl. No.: 09/743,075

(22) PCT Filed: Jul. 5, 1999

(86) PCT No.: PCT/FR99/01616
§ 371 (c)(1),
(2), (4) Date: Feb. 14, 2002

(87) PCT Pub. No.: WO00/01395
PCT Pub. Date: Jan. 13, 2000

(30) Foreign Application Priority Data

Jul. 3, 1998 (FR) ............................... 98 08568

(51) Int. Cl.$^7$ .................................................. A61F 2/02
(52) U.S. Cl. ....................................................... 424/423
(58) Field of Search ................................ 424/423, 680, 424/600, 602, 615, 709, 682, 683

(56) References Cited

U.S. PATENT DOCUMENTS 5,466,680 A 11/1995 Rudy
6,451,352 B1 * 9/2002 Yvin et al. .................. 424/680

FOREIGN PATENT DOCUMENTS

FR 2735980 1/1997

* cited by examiner

Primary Examiner—Carlos A. Azpuru
(74) Attorney, Agent, or Firm—Kilpatrick Stockton LLP

(57) ABSTRACT

The present invention provides novel hypoosmotic saline compositions and their use as medicines for the prevention of the release of chemical mediators responsible for triggering phenomena causing inflammation of mucous membranes, and for the dissolution of cerumen plugs located in the external auditory meatus.

14 Claims, 2 Drawing Sheets

HYPOOSMOTIC SALINE SOLUTIONS, METHOD FOR PREPARING SAME AND MEDICINES BASED ON SAID SOLUTION

CROSS-REFERENCE TO RELATED APPLICATIONS

The present application is a U.S. national phase application under 35 U.S.C. § 371 of PCT/FR99/01616 filed Jul. 5, 1999 which claims priority to French patent application No. 98/08568 filed Jul. 3, 1998.

BACKGROUND OF INVENTION

FIELD OF THE INVENTION

BRIEF SUMMARY OF THE INVENTION

The subject of the invention is saline solutions.

It also relates to their method of preparation and the medicines based on these solutions.

Saline solutions and their use as medicines are already known.

There may be mentioned, in this regard, physiological saline and solutions of isotonic sea water; these products are used, inter alia, for washing wounds, the eyes and the nasal fossae blocked by mucous or mucopurulent secretions.

The Applicant Company has developed novel saline solutions.

These novel saline solutions are characterized in that they are hypoosmotic and in that they have:

a pH of 7.0 to 8.30, a resistivity of 52 to 370 $\Omega$ and preferably of 57 to 85 $\Omega$, a density of 1.002 to 1.008, a dry matter content of 0.5% to 1%, an osmolarity of between 100 mOs and 305 mOs/kg (milliosmol/kg), preferably between 140 and 240 mOs/kg, and a chemical constitution of which the principal elements result from Table I below:

TABLE I

| Sodium (Na) | from 600 to 2000 mg/l |
|---|---|
| Potassium (K) | from 6 to 40 mg/l |
| Chlorides (Cl) | from 2000 to 5800 mg/l |
| Calcium (Ca) | from 200 to 300 mg/l |
| Magnesium (Mg) | from 1000 to 1200 mg/l |
| Sulfates ($SO_4$) | from 2000 to 3000 mg/l |

The invention also relates to the use, as medicine, of saline solutions in accordance with the invention.

Its subject is therefore medicines or pharmaceutical compositions, characterized in that they are based on hypoosmotic saline solutions in accordance with the invention.

More particularly, the subject of the invention is the use of the hypoosmotic saline solutions in accordance with the invention for the production of a medicine intended for a treatment suitable for the prevention and for the limitation of the release, into the body, of the chemical mediators responsible for triggering the phenomena causing inflammation of the mucous membranes in general and more particularly of the mucous membranes of the respiratory, in particular nasal and bronchial, tracts, of the buccal, vaginal, intestinal and anal mucous membranes.

It has been found that the chemical mediators in question are released under the influence of pro-inflammatory agents which, in the case in particular of the respiratory and buccal tracts, form part of the group comprising substances of bacterial origin, viruses, bacteria, pollen and other irritant and allergenic constituents transported by the air inhaled.

The subject of the invention is also the use of the hypoosmotic saline solutions in accordance with the invention for the production of medicines intended for the cerumenolytic treatment of the external auditory canal, in other words for the dissolving treatment of cerumen plugs.

The subject of the invention is also:

a medicament based on a hypoosmotic saline solution as claimed in the invention, suitable for preventing and limiting the release, under the influence of substances of bacterial origin, viruses, bacteria, pollen and other irritant and allergenic constituents transported by the air inhaled, of the chemical mediators responsible for triggering the phenomena causing inflammation of the mucous membranes in general and more particularly of the mucous membranes of the respiratory, in particular nasal and bronchial, tracts, of the buccal, vaginal, intestinal and anal mucous membranes, and a cerumenolytic medicine based on a hypo-osmotic saline solution as claimed in the invention.

DETAILED DESCRIPTION OF THE INVENTION

Figure 1:
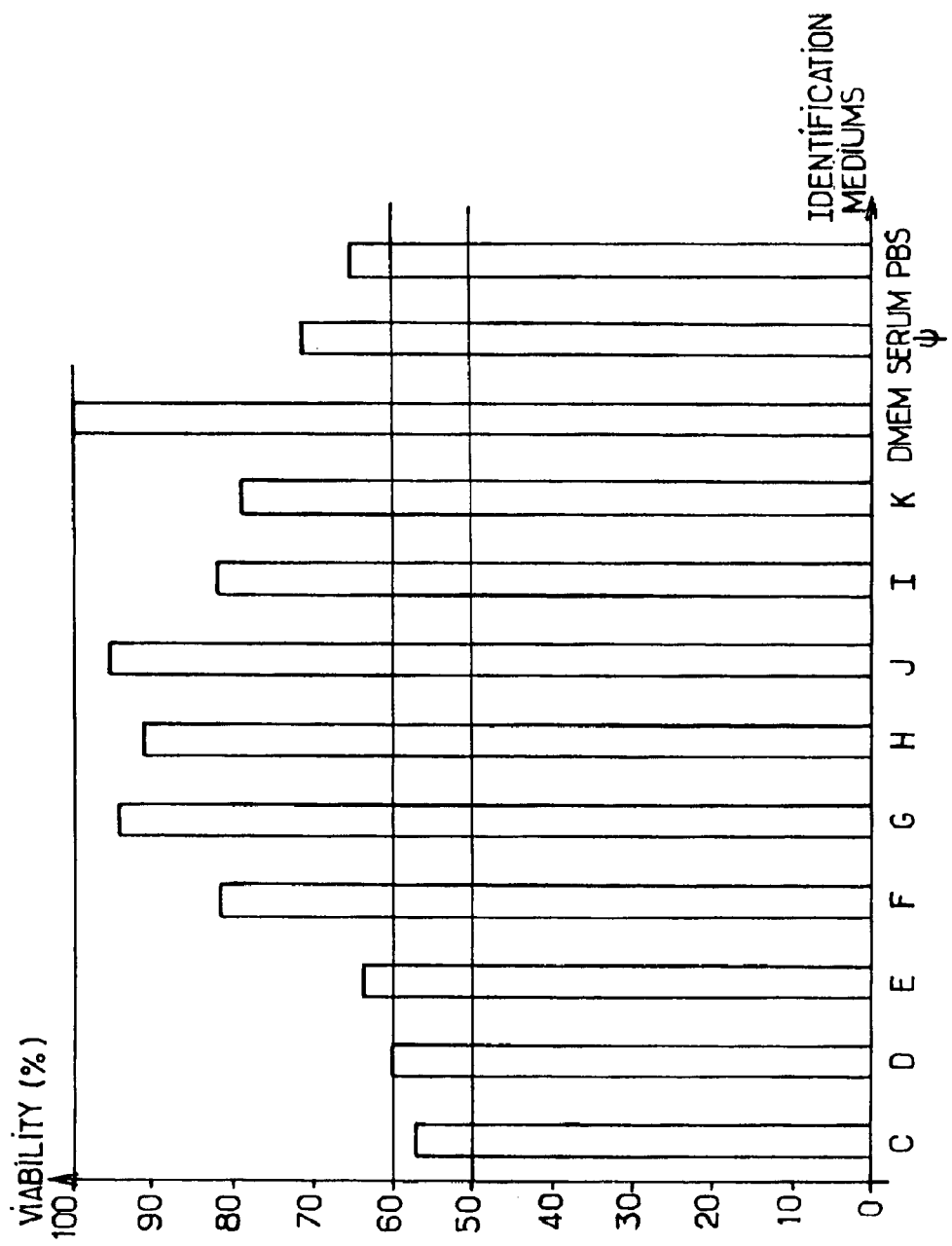
FIG. 1 demonstrates the effects of solutions described in Table III on viability of cells in vitro after 16 hours of contact.

To prepare the hypoosmotic solutions in accordance with the invention, the procedure can be carried out as indicated below.

Sea water, preferably collected at a depth of 5 to 10 meters, in a zone with strong movements of current, and characterized by a salt content greater than 32 g/l is used as raw material.

This water is analyzed, allowed to settle and then rapidly:

subjected to sodium-salt removal by the electrodialysis technique until the osmolarity is brought to a value of between 100 and 305 mOs/kg, filtered, stored under sterile conditions, in particular in a stainless steel tank.

It is again analyzed at this stage in order to verify:

its sterility, its osmolarity.

Finally, it can be packaged under sterile conditions on premises specially treated under a controlled atmosphere.

The work which has made it possible to illustrate certain aspects of the invention include experiments relating to the capacity of the hypoosmotic saline solutions in accordance with the invention to prevent and to limit the release of the chemical mediators responsible for triggering the phenomena causing inflammation of the mucous membranes of the respiratory tracts; these experiments show the superiority of the hypoosmotic saline solutions in accordance with the invention compared with three well known reference products, namely physiological saline, PBS buffer and isotonic sea water.

This superiority is manifested both by a lower toxicity and by an improved activity from the point of view of the desired effects.

The respective toxicities of the hypoosmotic saline solutions in accordance with the invention, of physiological saline, of PBS buffer and of isotonic sea water were defined by means of a comparative study relating to the viability of human respiratory cells, that is to say cells which are found in the respiratory mucous membranes, in the presence of the hypoosmotic solutions, on the one hand, and of the three reference products, on the other hand.

To carry out this study, human respiratory glandular epithelial cells obtained from bronchial samples were used.

These respiratory epithelial cells were inoculated at the same cell density in 12-well culture plates.

They were cultured for 48 hours in DMEM/F12 culture medium supplemented, on the one hand, with 2% of a nutrient consisting of the product marketed under the trademark ULTROSER G and, on the other hand, with a sufficient dose of antibiotics to avoid bacterial contamination; confluent and homogeneous cultures in a monolayer are thus obtained, that is 310 000 cells per culture well after 48 hours of culture.

When confluence is reached, the cells are washed with a physiological saline solution (PBS/$Ca^{2+}$, pH 7.4) and brought into contact, on the one hand, with eight hypoosmotic saline solutions in accordance with the invention and, on the other hand, with the three reference products consisting of physiological saline, PBS buffer and isotonic sea water designated K; the abovementioned reference cell culture medium known by the name DMEM/F12 was also used.

The eight hypoosmotic solutions tested are characterized, respectively, by resistivity values equal to 57.30 Ω, 64.93 Ω, 74.34 Ω, 84.90 Ω, 107 Ω, 134.40 Ω, 192.30 Ω and 361 Ω and designated by the letters J, I, H, G, F, E, D and C, respectively.

The main constituent elements of the hypoosmotic solutions G, H, I and J are presented in Table II below.

TABLE II

| Constituents | Units | G | H | I | J |
| --- | --- | --- | --- | --- | --- |
| Sodium (Na) | mg/l | 600 | 765 | 1130 | 1370 |
| Potassium (K) | mg/l | 6.9 | 11.2 | 20.8 | 27.4 |
| Chlorides (Cl) | mg/l | 2556 | 2930 | 3797 | 4248 |
| Calcium (Ca) | mg/l | 265 | 290 | 310 | 330 |
| Magnesium (Mg) | mg/l | 1100 | 1130 | 1200 | 1200 |
| Sulfates ($SO_4$) | mg/l | 2570 | 2570 | 2570 | 2600 |

At the end of several periods of incubation, that is to say of cellular contact, namely 16 hours and 24 hours, cell viability was evaluated in the presence of the media which have just been mentioned.

This cell viability is expressed by the percentage of viable cells at the end of each period of incubation in the hypoosmotic saline solutions as claimed in the invention, in physiological saline, in PBS buffer and in the K medium, relative to the number of viable cells in the DMEM/F12 culture medium serving as reference medium.

It was evaluated with the aid of the so-called Trypan blue, in solution at 0.4%, exclusion test followed by cell counting with a Malassez cell.

In accordance with the test in question, the cells are detached from the culture support using trypsin; the live cells are then counted in an aqueous solution containing 0.4% Trypan blue; indeed, Trypan blue is a cellular dye which does not penetrate inside a live cell; only the nonviable cells allow entry of Trypan blue.

The number of live cells in the DMEM/F12 culture medium being by definition expressed relative to 100, it is possible to express the cell viability in the other media, as a percentage relative to said culture medium.

Figure 2:
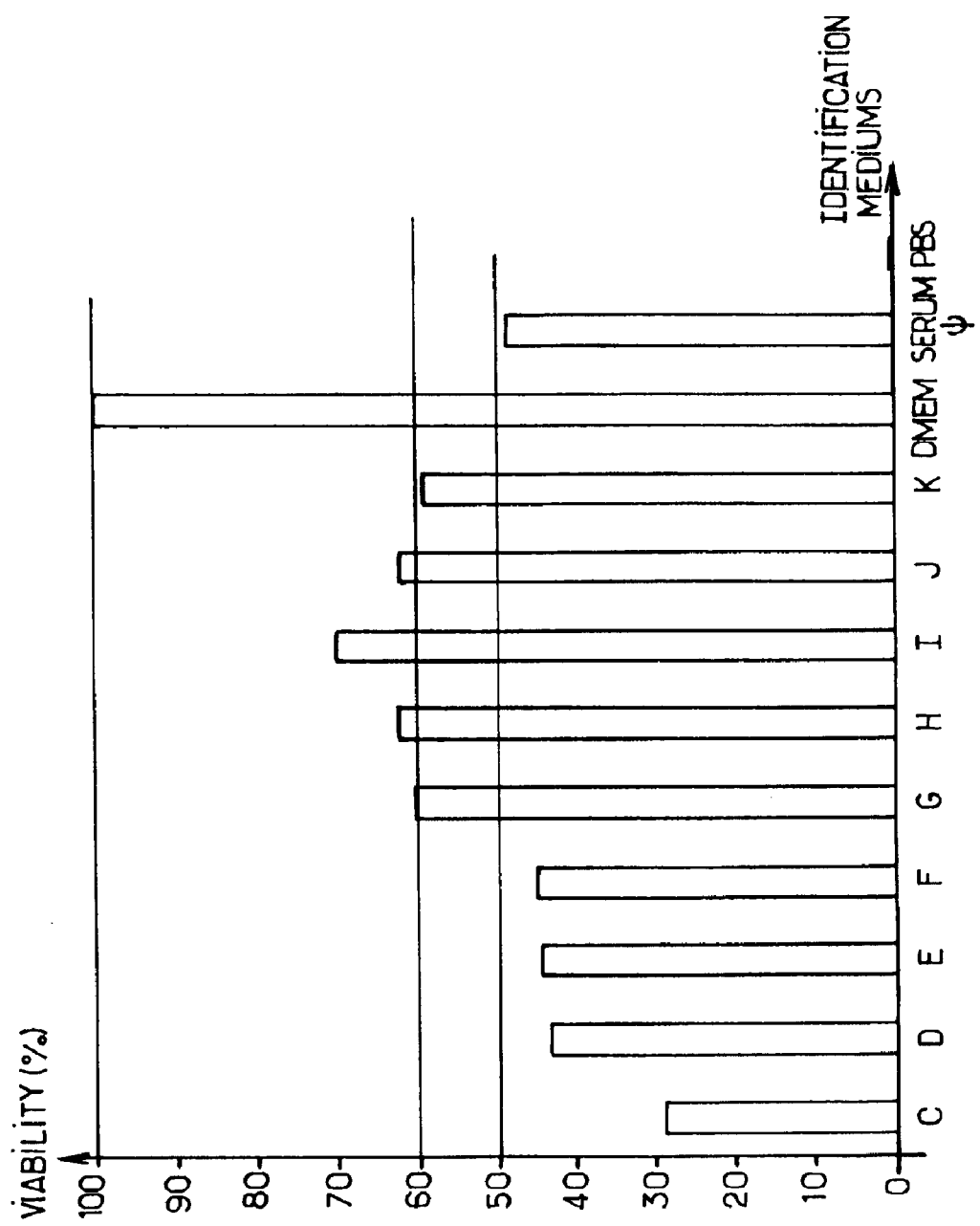
FIG. 2 demonstrates the effects of solutions described in Table III on viability of cells in vitro after 24 hours of contact.

The results recorded are assembled in FIGS. 1 and 2 which show, respectively, the results recorded after 16 hours and 24 hours of contact, namely the percentage of live cells after contact with each of the hypoosmotic solutions in accordance with the invention and each of the reference products, it being recalled that the viability in the DMEM/F12 culture medium is 100%.

The percentages in question are also assembled in Table III:

TABLE III

| | Percentage of viable cells | | | | | | | | | | |
| --- | --- | --- | --- | --- | --- | --- | --- | --- | --- | --- | --- |
| | C | D | E | F | G | H | I | J | K | DMEM | Physiological saline | PBS |
| 16 hours | 57 | 60 | 64 | 80 | 94 | 91 | 95 | 82 | 79 | 100 | 72 | 66 |
| 24 hours | 29 | 43 | 44 | 45 | 60 | 62 | 70 | 62 | 59 | 100 | 49 | 0 |

Examination of FIGS. 1 and 2 and of the values assembled in Table III shows that the preferred hypoosmotic saline solutions in accordance with the invention are solutions G, H, I and J which, over incubation periods of 16 and 24 hours, allow better cell viability than the reference products.

For the demonstration of the capacity of the hypoosmotic saline solutions in accordance with the invention to prevent and to limit the release, under the influence of pro-inflammatory agents comprising substances of bacterial origin, viruses, bacteria and any other irritant and allergenic constituents transported by the air inhaled, of the chemical mediators responsible for triggering the phenomena causing inflammation of the mucous membranes of the human respiratory tracts, cell cultures obtained from the mucous membranes in question are subjected to a combination of experiments comprising a step of bringing into contact with pro-inflammatory agents and a step of incubating the cell cultures thus treated in a control medium, in reference media and in the hypoosmotic solutions as claimed in the invention.

It has been shown more particularly that, under the action of certain pro-inflammatory agents of bacterial origin, such as for example the *P. aeruginosa* lipopolysaccharide or LPS, serotype 10, used at the concentration of 1 μg/ml, the human respiratory, glandular, epithelial cells release chemical mediators such as interleukin-8, which trigger the inflammatory phenomena.

And the Applicant Company has found, surprisingly and unexpectedly, that a high prevention and limitation of the release of chemical mediators, in this case interleukin-8, is obtained when, after stimulation by pro-inflammatory agents, the relevant cell cultures are incubated in the hypoosmotic saline solutions used as claimed in the invention.

The abovementioned experiments were carried out on cultures of glandular secretory cells isolated from the human bronchial submucosa.

The cells in question are cultured in a medium consisting, for example, of that known under the name RPMI 1640; this medium is supplemented with 2% of ULTROSER G medium; when the cultures have reached 90% confluence, the pro-inflammatory agent identified above is introduced and then the culture medium is removed.

After washing the cells thus treated, they are incubated:
in the same RPMI 1640 culture medium alone which acts as control medium,
in physiological saline (reference medium),
in isotonic sea water (reference medium),
in the hypoosmotic saline solutions as claimed in the invention identified above and designated H, I and J.

The production of interleukin-8 by the glandular epithelial cells is estimated by the ELISA assay method (using the assay kit sold under the trademark MEDGENIX DIAGNOSTIC, Belgium) after a contact time of one hour in the supernatants of the media identified above.

The results recorded, on the one hand, for the three hypoosmotic solutions H, I and J in accordance with the invention and, on the other hand, for the DMEM/F12 culture medium, as well as for the reference media, namely physiological saline and isotonic sea water, are:

282 pg/ml/hour in the case of the DMEM/F12 medium,
76 pg/ml/hour in the case of physiological saline,
42 pg/ml/hour in the case of isotonic sea water,
29 pg/ml/hour in the case of solution J,
16 pg/ml/hour in the case of solution I, and
7 pg/ml/hour in the case of solution H.

These results show the superiority of the solutions in accordance with the invention from the point of view of their capacity to prevent and to limit the release, under the influence of pro-inflammatory agents, of the chemical mediators responsible for triggering the phenomena causing inflammation of the mucous membranes.

It was possible to confirm these results by experiments carried out on the culture of a cell line of the surface respiratory epithelium (respiratory line 16-HBE).

In practice, and in the context of their use for the production of the medicines which have just been mentioned, the hypoosmotic saline solutions in accordance with the invention may be administered in the form of aerosols or of nebulisates or by instillation in the form of drops.

This includes pharmaceutical or medicinal compositions intended for treatment which prevents and limits the release of the chemical mediators responsible for triggering the phenomena causing inflammation of the mucous membranes of the human respiratory tracts which occur in rhinopharyngeal and pulmonary conditions.

The hypoosmotic saline solutions in accordance with the invention may be provided in the form of aerosols for nasal or buccal administration with local action exerting its effect on the mucous membranes of the human respiratory tracts, in particular at the level of the nasal fossae and of the bronchi.

The usual dosage may be 2 puffs about thirty seconds apart, repeated two to three times per day as a buccal inhalation depending on the condition and the age of the patient.

In the case of a nasal inhalation, it is usually one to two puffs into each nostril 3 to 4 times per day depending on the condition and age of the patient.

It is also possible to envisage using the hypoosmotic solutions in accordance with the invention as they are for preventing and limiting the release of the chemical mediators responsible for triggering the inflammatory phenomena in the case of the buccal, vaginal, intestinal and anal mucous membranes.

The dosage will be adjusted as claimed in the type of condition treated.

In the context of their use for the production of medicines for the cerumenolytic treatment of the external auditory canal, being cerumenolytic medicines in this case, the hypoosmotic saline solutions in accordance with the invention may be applied by spraying or by instillation in the form of drops into the external auditory canal of the ear.

In the presence of cerumen plugs, they can be advantageously applied at the rate of two daily sprayings or instillations for a period of 3 to 4 days.

For regular hygiene, they can be advantageously applied two to three times per week, and more in the case of those carrying hearing aids, so as to promote good operation of the device.

What is claimed is:

1. A hypo-osmotic saline solution comprising:
   a pH of 7.0 to 8.30;
   a resistivity of 52 to 370;
   a density of 1.002 to 1.008;
   a dry matter content of 0.5% to 1%;
   an osmolarity between 100 mOs and 305 mOs/kg; and,
   a chemical composition of which the principal elements consist of:
   sodium (Na) in an amount from 600 to 2000 mg/l;
   potassium (K) in an amount from 6 to 40 mg/l;
   chlorides (Cl) in an amount from 2000 to 5800 mg/l;
   calcium (Ca) in an amount from 200 to 300 mg/l;
   magnesium (Mg) in an amount from 1000 to 1200 mg/l; and,
   sulfates ($SO_4$) in an amount from 2000 to 3000 mg/l.

2. A medicine based on a hypo-osmotic saline solution as claimed in claim 1 suitable for preventing and limiting the release, into the body, of the chemical mediators responsible for triggering the phenomena causing inflammation of the mucous membranes in general and more particularly of the mucous membranes of the respiratory, in particular nasal and bronchial, tracts, of the buccal, vaginal, intestinal and anal mucous membranes.

3. A medicine based on a hypo-osmotic saline solution as claimed in claim 1, suitable for preventing and limiting the release, under the influence of substances of bacterial origin, viruses, bacteria, pollen and other irritant and allergenic constituents transported by the air inhaled, of the chemical mediators responsible for triggering the phenomena causing inflammation of the mucous membranes of the human respiratory tracts.

4. A cerumenolytic medicine based on a hypo-osmotic saline solution as claimed in claim 1.

5. A method of preparing the hypo-osmotic saline solutions as claimed in claim 1, characterized in that, successively,
   there is collected as raw material, sea water having a salts content greater than 32 g/l, advantageously at a depth of 5 to 10 meters in a zone with strong movements of current,
   this water is analyzed and allowed to settle,
   sodium-salt is removed from the water, which has been allowed to settle, by the electrodialysis technique until its osmolarity is brought to a value of between 100 and 305 mOs/kg,
   the medium is filtered, and
   the product obtained is stored under sterile conditions in a stainless steel tank.

6. The hypo-osmotic saline solution of claim 1 having an osmolarity between 140 and 240 mOs/kg.

7. The hypo-osmotic saline solution of claim 1 having a resistivity of 57 to 85.

8. A medicine comprising hypo-osmotic saline solution comprising:
- a pH of 7.0 to 8.30;
- a resistivity of 52 to 370;
- a density of 1.002 to 1.008;
- a dry matter content of 0.5% to 1%;
- an osmolarity between 100 mOs and 305 mOs/kg; and,
- a chemical constitution of which the principal elements consist of:
   - sodium (Na) in an amount from 600 to 2000 mg/l;
   - potassium (K) in an amount from 6 to 40 mg/l;
   - chlorides (Cl) in an amount from 2000 to 5800 mg/l;
   - calcium (Ca) in an amount from 200 to 300 mg/l;
   - magnesium (Mg) in an amount from 1000 to 1200 mg/l; and,
   - sulfates ($SO_4$) in an amount from 2000 to 3000 mg/l.

9. The medicine of claim 8 having an osmolarity between 140 and 240 mOs/kg.

10. The medicine of claim 8 having a resistivity of 57 to 85.

11. A method for preventing and limiting release of chemical mediators responsible for triggering phenomena causing inflammation of mucous membranes in a patient comprising administering to the patient the saline solution of claim 1.

12. A method for preventing and limiting release of chemical mediators responsible for triggering phenomena causing inflammation of mucous membranes in a patient comprising administering to the patient the saline solution of claim 1, wherein the mucous membranes are nasal, bronchial, buccal, vaginal, intestinal or anal mucous membranes.

13. A method for preventing and limiting release of chemical mediators responsible for triggering phenomena causing inflammation of mucous membranes of a patient's respiratory tract, wherein the release of the chemical mediators is influenced by substances of bacterial origin, viruses, bacteria, pollen and other irritant and allergenic constituents transported by inhaled air, comprising administering to the patient the saline solution of claim 1.

14. A method for dissolving a cerumen plug comprising administering the saline solution of claim 1 an external auditory canal of a patient having the cerumen plug.

* * * * *